United States Patent [19]

Birkle

[11] Patent Number: 5,030,010
[45] Date of Patent: Jul. 9, 1991

[54] PROCESS FOR THE OPTICAL SCANNING OF AN OBJECT AND DEVICE FOR THE IMPLEMENTATION OF SAID PROCESS

[76] Inventor: Gebhard Birkle, Inselgasse 16, D-7750 Konstanz, Fed. Rep. of Germany

[21] Appl. No.: 408,506

[22] PCT Filed: Feb. 16, 1988

[86] PCT No.: PCT/DE88/00075
§ 371 Date: Oct. 16, 1989
§ 102(e) Date: Oct. 16, 1989

[87] PCT Pub. No.: WO88/06325
PCT Pub. Date: Aug. 25, 1988

[30] Foreign Application Priority Data

Feb. 17, 1987 [DE] Fed. Rep. of Germany ....... 3704960
Feb. 17, 1987 [DE] Fed. Rep. of Germany ....... 8702417

[51] Int. Cl.$^5$ .......................... G02B 26/10; G02B 6/00
[52] U.S. Cl. .............................. 356/445; 250/227.25; 350/96.32
[58] Field of Search .......................... 356/445, 447, 448; 250/227.25; 350/96.32

[56] References Cited

U.S. PATENT DOCUMENTS

| | | | |
|---|---|---|---|
| 3,461,856 | 8/1969 | Polanyi | 356/41 |
| 3,843,865 | 10/1974 | Nath | 219/121 L |
| 3,947,088 | 3/1976 | French | 356/448 |
| 3,995,934 | 12/1976 | Nath | 350/96.32 |
| 4,236,784 | 12/1980 | Palmer | 350/96.20 |

FOREIGN PATENT DOCUMENTS 0197673 10/1986 European Pat. Off. .
1598004 12/1970 Fed. Rep. of Germany .

OTHER PUBLICATIONS

Taylor. "Liquid Optical Fibers" *Applied Optics*, vol. 11, No. 4 (Apr. 1972) pp. 786-790.
J. C. Mtzler & A. T. Montibello, "Variable Optical Read Head", IBM Technical Disclosure Bulletin; vol. 18, No. 10, pp. 3277-3280 (Mar. 1976).

Primary Examiner—Richard A. Rosenberger
Attorney, Agent, or Firm—Peter K. Kontler

[57] ABSTRACT

A device for optically scanning an object includes a nozzle which is connected to a source of pressurized liquid. The nozzle generates a liquid stream which can be directed at the object. The device further includes a laser which is arranged to direct a beam of light at the object in order to scan the latter, and a sensor for receiving and analyzing light reflected from the object. The laser and the nozzle are positioned relative to one another in such a manner that light reflected from the object enters the liquid stream which then conducts the reflected light to the nozzle. The nozzle is connected to the sensor by at least one optical fiber which functions to conduct the reflected light from the nozzle to the sensor. One or more additional optical fibers may be provided to conduct light from the laser to the nozzle. The liquid stream then serves not only to conduct reflected light from the object to the nozzle but also to conduct the light used for scanning from the nozzle to the object.

12 Claims, 4 Drawing Sheets

PROCESS FOR THE OPTICAL SCANNING OF AN OBJECT AND DEVICE FOR THE IMPLEMENTATION OF SAID PROCESS

TECHNICAL FIELD

The invention relates to a process, according to the preamble of claim 1, for the optical scanning of an object as well as a device for carrying out the process.

PRIOR ART

It is known to use linear and mechanical light deflectors which cause angular deflection for the optical detection or measurement of objects and their surfaces. Relative motion of the light and the surface to be scanned is required if an action or a change is to be observed in the x-y plane. In contact activated or quasi-contact activated object scanning a light conductor can simultaneously serve for light transmission to the object and receiving transmissions to the sensor, as well as for image point definition. Particularly in conjunction with flexible optic fibers, the range of application of tuned detection systems is expanded to include a scanning principle having many variations, e.g., in the detection of bar codes or when OCR reading instruments are employed.

In many applications, however contact with an object or quasi-contact by a solid light conductor is not possible. In critical environments, e.g., in the presence of high temperatures or humidity, or aggressive media such as dust, smoke, vapor, interfering light or radioactivity, or interfering surface coatings due to liquid, dust, foam or other substances, it is not possible to use solid light conductors. Similarly, the use of solid light conductors is excluded in the optical scanning of objects having a critical consistency or geometry such as powdered or particulate products, products with a fibrous surface structure, secreting organic substances or fluids enriched with suspended substances.

An optical probe for applying a light cable to an object is known from the West German Offenlegungsschrift 15 98 004 and consists of a transparent, balloon-like and flexible membrane filled with a light conducting liquid which can be replenished via a reservoir and a supply line in order to maintain a specified static pressure in the balloon. A bundle of optical fibers whose ends are disposed in the liquid before the membrane opens into, and forms a seal with, the balloon. Light can be thrown onto an object via the optical fibers, the liquid and the membrane and then reflected and conducted back to a receiving station through the membrane, the liquid and the optical fibers. With such a device, however, it is not possible to perform an optical scan in the above-mentioned critical environment.

TECHNICAL OBJECT

It is accordingly an object of the invention to provide a process and a device for the optical scanning of an object which cannot be subjected to a contactless scan, or to a contact-activated scan, using a solid light conductor, because the object is in a critical environment, or is provided with interfering surface coatings, or has a consistency or geometry which does not permit contactless or contact-activated scanning by means of a solid light conductor.

DESCRIPTION OF THE INVENTION

According to the invention, the solution to this object is in the features of the process of claim 1; devices for carrying out the process are characterized in claims 3 and 13. Additional advantageous embodiments of the invention are contained in the remaining subclaims.

The invention has the great advantage that by means of the same, optical object scanning is possible even for those applications where contactless scanning with light only, or contact-activated scanning using a solid light conductor, was not possible until now. Thus, the "gist" of the invention is that the combination of a solid light conductor and a liquid light conductor in the form of a liquid stream serves as a light conductor. The transmitted light beam or light ray is incorporated in the liquid stream in a coupling station and is now directed onto the surface of the object to be scanned together with the liquid stream. After impingement of the liquid stream upon the impingement point, the transmitted light is at least partially reflected, conducted back within the liquid stream counter to the flow direction and separated from the liquid stream. The index of refraction of the liquid is advantageously taken into account in the coupling station, e.g., by appropriate selection and design of an optical system as a coupling station. This mode of object scanning is accordingly contact-activated object scanning in which the scanning light conductor is a more or less fine liquid stream whose liquid is regenerated or can be disposed of.

By using the liquid stream as a light conductor, the contact-activated object scanning can occur in a critical environment, e.g., at high temperatures and humidity levels, in aggressive media such as dust, smoke, vapor or interfering light, or even in the presence of radioactivity. The invention is intended especially for the optical scanning of objects having interfering surface coatings which can be removed for a period of time or continuously by means of a liquid stream, e.g., liquid, dust or foam present on the surface of the object are washed away therefrom by the impingement pressure of the liquid stream. Similarly, the scanning of objects having a critical consistency or geometry is possible using the invention, e.g., the scanning of powdered or particulate material, bulk materials, objects having a fibrous surface structure, secreting organic substances or liquids containing suspended substances.

Advantageously, the liquid stream determines the size and position of the scanning point on the object. It is necessary to ensure that the liquid used is light conductive for the wavelength of the light employed. The liquid light conductor can accordingly serve both as a light conductor to the object and as a return conductor for the reflected light to signal processing.

In principle, it is possible to direct the transmitted light, outside of the liquid stream, onto the impingement point of the latter on the object and to incorporate reflected light in the liquid stream at the impingement point for return conduction.

BRIEF DESCRIPTION OF THE DRAWING

Examples of the invention are displayed in the drawing and described below with the following illustrations showing.

MODES OF EXECUTING THE INVENTION

Figure 1:
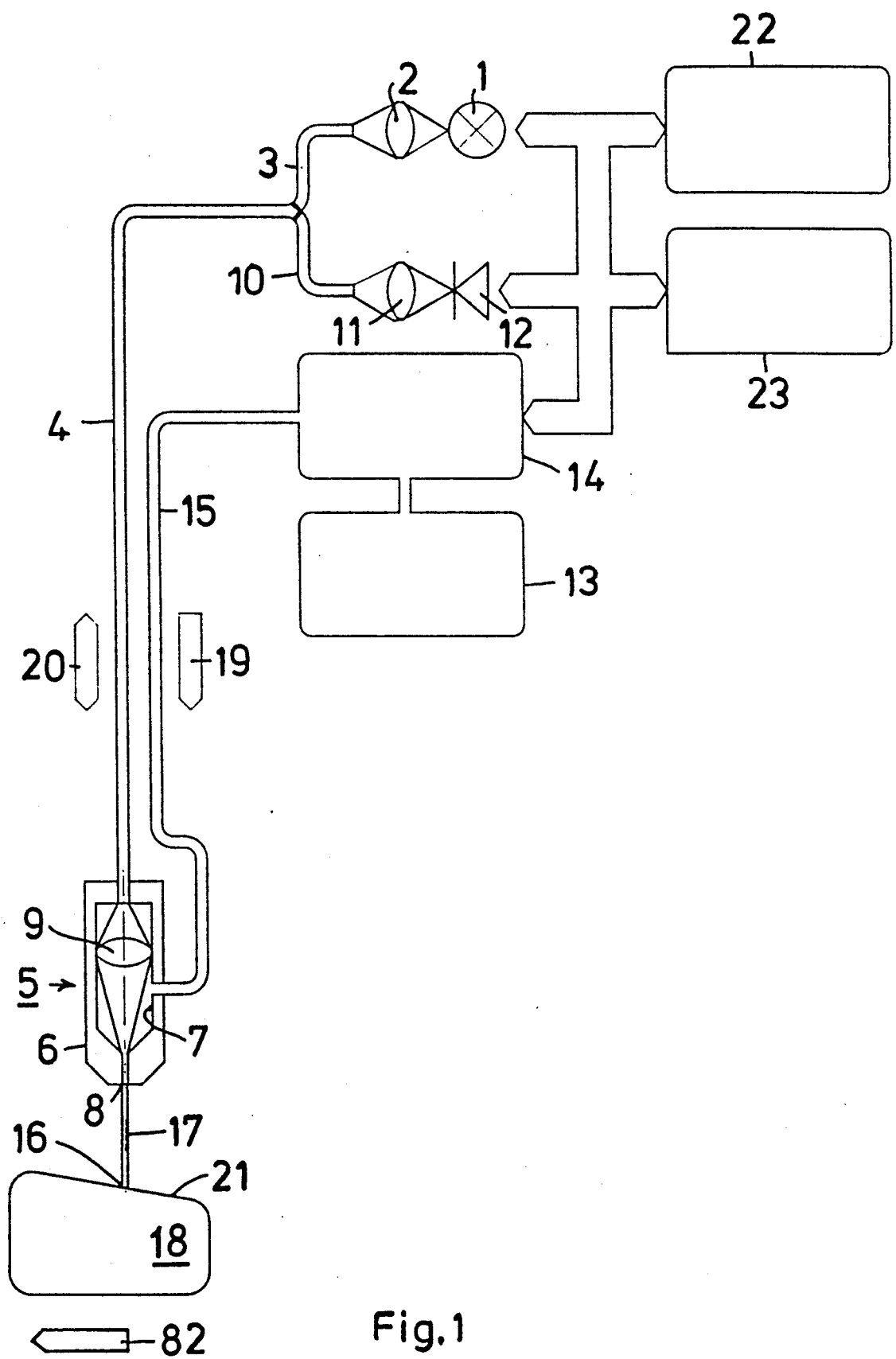
FIG. 1 a schematic illustration of a device for carrying out the process of the invention and having solid light conductors, e.g., flexible optical fibers, between the scanning head and the light source, FIG. 2a a diagrammatic layout of the device consisting of a scanning head, conveying system, light source and sensor with the last two being connected to the scanning head by a solid light conductor, FIG. 2b an embodiment of the device of FIG. 2a in which the solid light conductor serves for back-and-forth conduction of the light from the scanning head, FIG. 2c a device according to FIG. 2a in which the light source and the sensor are inside the scanning head, FIG. 3 a device with two scanning heads each of which generates a liquid stream, one serving for outward conduction of the transmitted light beam and the other for return conduction of the reflected light beam, the supply of the scanning heads corresponding to that in FIG. 2a, FIG. 4 a device for the production of a liquid stream, the transmitted light being directed onto the impingement point from outside of the liquid stream and reflected light being conducted back within the liquid stream, FIG. 5 a device with a manifold scanning head for the production of a plurality of liquid streams each of which has a light source, a sensor panel and a supply line from a common conveying system associated therewith, FIG. 6 a technical exemplary embodiment of a device according to FIG. 1, FIG. 7 a plan view of the end face of the common fiber bundle for the transmitting and receiving fibers in the scanning head of FIG. 6, FIG. 8 the design of a scanning head as a tube for inspecting the interiors of objects, FIG. 9 the design of a scanning as a flexible hose for inspecting the interiors of cavities such as, for example, tubes and FIG. 10 the deflection of the liquid stream with an electrical or mechanical deflecting instrument in order to produce relative motion between the scanning point and the object by controlled movement of the liquid stream over the object.

FIG. 1 shows a diagrammatic layout of a device for the optical scanning of an object by means of a liquid stream produced from light-conducting liquid. The liquid stream is hereafter referred to as the scanning stream. A light source 1, which can be a laser light source, generates a light beam which is focused and delivered to a solid light conductor by an optical system. The term "optical system" will be understood generally to include an appropriately arranged and designed module which is capable of generating an optical effect such as projection, enlargement, focusing and the like. "Light conductor" will be understood, in particular, to encompass solid optical fibers which can be either transmitting fibers or receiving fibers. "Nozzle" will be understood to mean an appliance which can generate a liquid stream mechanically as well as electrically or magnetically.

The transmitting fiber 3 is guided, in a flexible cable 4, to a scanning head 5 consisting, for example, of a cylindrical housing 6 which surrounds a cavity 7. The lower end of the housing 6 has a fine opening 8 which constitutes a nozzle, for instance. An optical system 9 is disposed in the cavity 7 of the scanning head 5 in the upper region thereof. Similarly, at least one receiving fiber 10 is guided within the cable 4 and, like the transmitting fiber 3, ends inside the scanning head 5 and above the optical system 9. The other end of the receiving fiber 3 is disposed opposite an optical system 11 and the latter is situated opposite an opto-electrical sensor 12 which can, for example, be a diode.

A liquid which is preferably light-conducting for the wavelength of the light being employed is located in a container 13. A conveying system 14 for the liquid is connected with the scanning head 5 by a liquid supply line 15 which opens into the cavity 7 of the housing 6. The liquid can be conveyed into the cavity 7 of the scanning head 5 via the conveying system 14. The conveying system can, in general, include a conveying pump or dosing pump, valves, pressure regulating means and filters. The scanning head can be supplied with the light-conducting liquid from a net or a tank or from the liquid environment surrounding the object. A scanning stream 17 is formed from the liquid by means of the conveying system 14 and the nozzle 8 and is directed onto an object 18 where it impinges the surface 21 of the object at an impingement point 16. A system supply unit 22 functions to supply the light source 1 as well as the sensor 12 and conveying system 14. The signals originating in the sensor 12 are processed in a signal processing instrument 23 and compared with a reference signal, for example.

The operation of the device is as follows:

Light-conducting liquid is conducted from the container 13 into the cavity 7 of the scanning head 5 by the conveying system 14 and is there pressed outwards through the nozzle 8 in the form of the fine scanning stream 17 by generating a pressure. This scanning stream is maintained throughout the entire scanning period. At the same time, a light beam is generated by the light source 1 and, after focusing on the transmitting fiber 3, is introduced into the volume of liquid within the cavity 7 via the optical system 9. The transmitted light is so focused by the optical system 9 that it is conducted directly outwards through the nozzle 8 together with the scanning stream 17. The scanning stream 17 serves as an additional, liquid light conductor. The light is reflected at the liquid/air boundary within the scanning stream 17 in accordance with the laws of optics and is conducted downwards within the scanning stream 17 to the impingement point 16 on the object 18.

At the impingement point 16, the transmitted light is at least partially reflected and conducted back within the scanning stream 17 so that, in this case, the scanning stream 17 simultaneously serves for outgoing and return conduction of the light. The reflected light is separated from the liquid by means of the optical system 9 and delivered to the receiving fiber 10 and thereafter falls, via the optical system 11, onto the sensor 12 whose electrical output signals are processed in the signal processing instrument 23. Upon movement of the object 18 in the direction of the motion arrow 82, which is to the left in FIG. 1, the surface 21 of the object 18 is scanned at the impingement point 16 in accordance with the movement.

Diagrammatic layouts of the device, which are designed similarly to the device of FIG. 1, are shown in FIGS. 2 to 5. FIG. 2a illustrates a scanning head 35 to which liquid 29 is conveyed by a liquid supply line 32. In the scanning head 25, the liquid is converted into a scanning stream 33 which is directed onto an object 24. A light source 27 is connected with the scanning head by a light conductor 30 and a sensor 28 is connected with the scanning head by a light conductor 31.

Figure 2A:
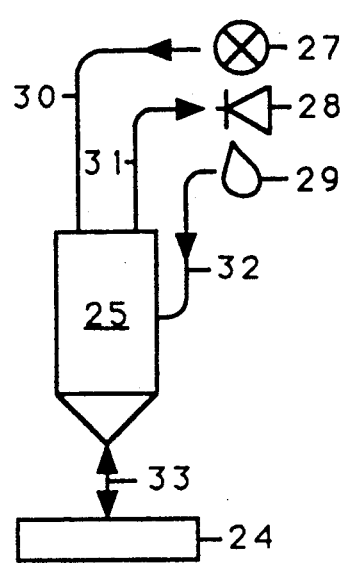
Figure 2B:
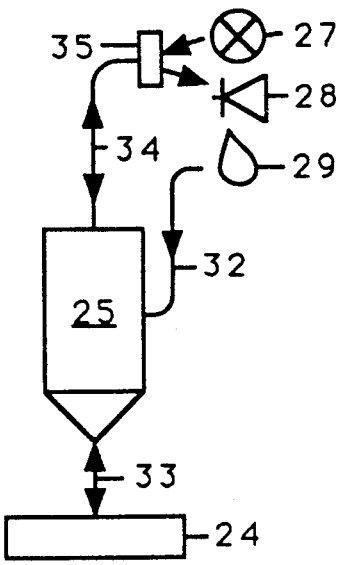
Figure 2C:
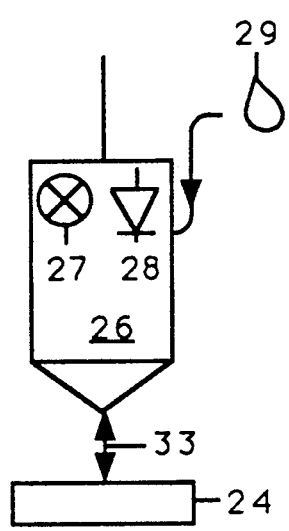

FIG. 2b shows a layout in which a light conductor 34 serves for both outgoing and return conduction of the light with the reflected light being deflected by a deflecting instrument 35 and delivered to the sensor 28. FIG. 2c shows another diagrammatic layout possibility in which the light source and the sensor 28 are located inside a scanning head 26. As in FIGS. 2a and 2b, the scanning head 26 is supplied with the scanning liquid 29 from a conveying system via a liquid supply line 32.

Figure 3:
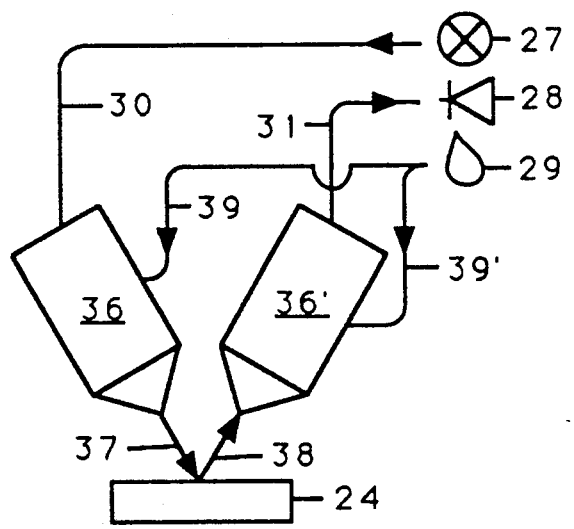

FIG. 3 illustrates a device having two scanning heads 36 and 36' which are arranged next to one another and are supplied with the scanning liquid 29 by means of respective liquid supply lines 39, 39'. Each scanning head 36, 36' generates a scanning stream 37, 38 and both scanning streams are directed towards a common impingement point on the object 24. The light is incorporated in the scanning stream 37 while reflected light, on the other hand, is incorporated in the second scanning stream 38 and conducted back.

Figure 4:
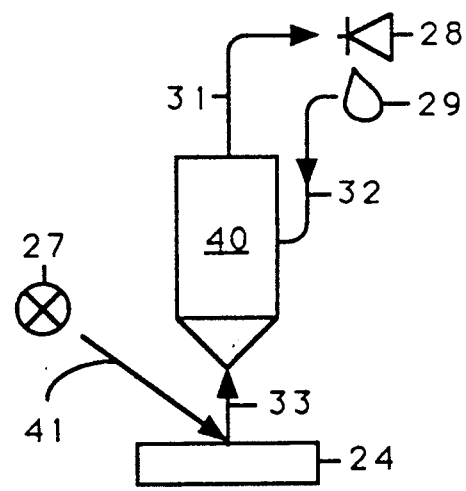

FIG. 4 shows a device in which only the liquid supply line 32 and the receiving light conductor 31 are led into the scanning head 40. A light beam 41 is pointed directly at the impingement point of the scanning stream 33 on the object 24 from outside the scanning stream and it is only the reflected light which is incorporated in the scanning stream 33 at the impingement point and conducted to the sensor 28 via the scanning head 40.

Figure 5:
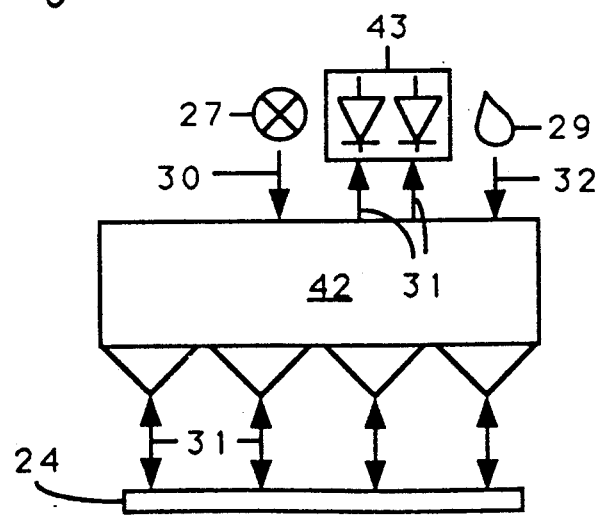

FIG. 5 illustrates a device having a manifold scanning head 42 which generates a plurality of scanning streams 33. Light issuing from the light source 27 can be incorporated in each scanning stream and return of the reflected light takes place as in FIG. 1 or 2. All of the return receiving conductors lead to a sensor panel 43 for appropriate further processing. The liquid supply line 32 for supplying the scanning liquid 29 from a conveying system functions to produce the plurality of scanning streams simultaneously.

Figure 6:
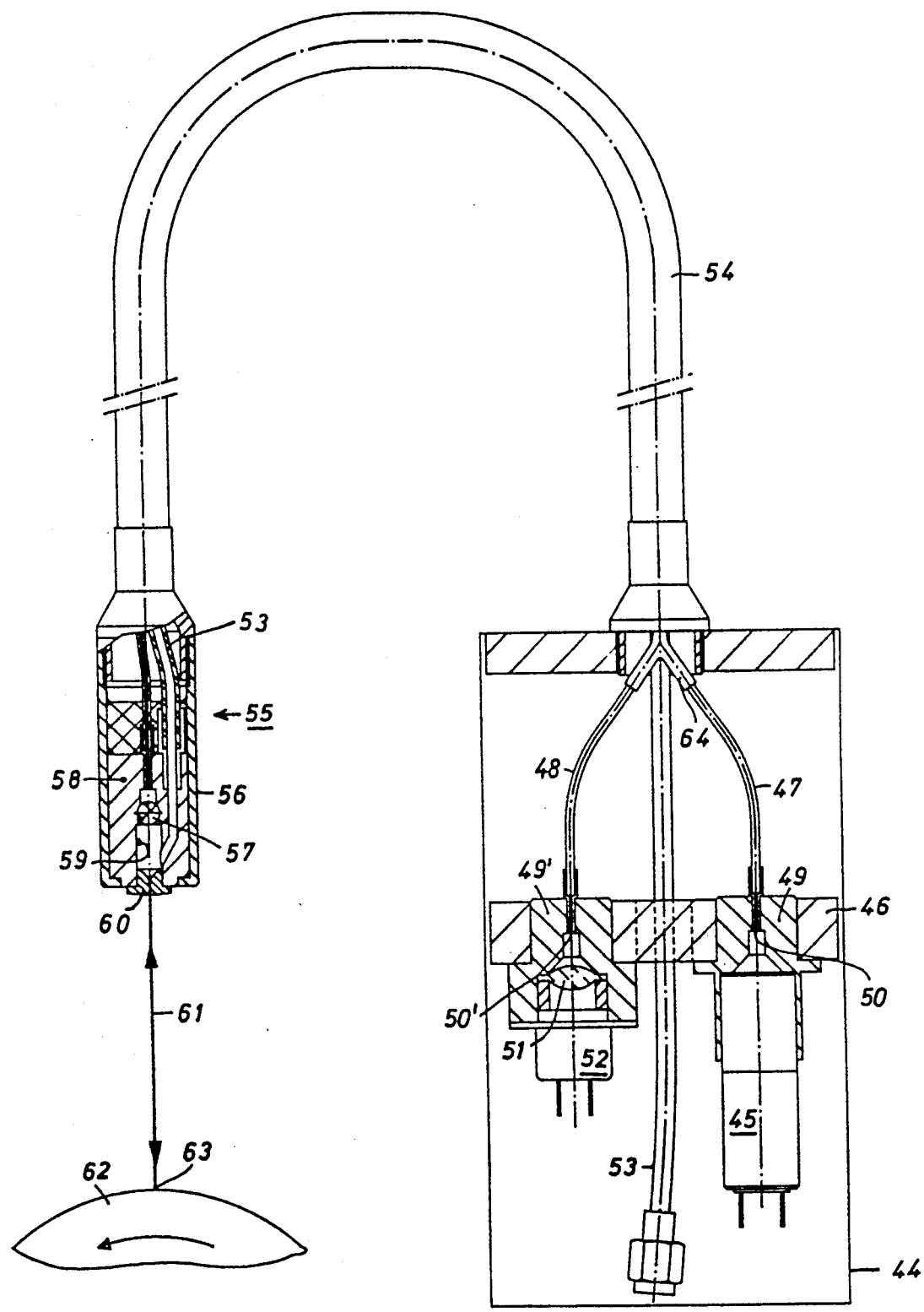

FIG. 6 shows a technical layout of the device according to the invention. A plate 46 is suitably arranged inside a detector housing 44 and a holder 49 is suitably mounted in or on the plate. On the one side of the plate 46, the holder 49 carries a diode laser within a coupling optical system 45. At least one transmitting fiber 47 leads into the holder 49 on the opposite side and is secured there. Similarly, another holder 29' is arranged in or on the plate 46 and an opto-electrical sensor 52 is disposed at one side of this holder 29'. At least one receiving fiber 48 enters the opposite side of the holder and an optical system 51 can be located between the end of the receiving fiber 48 and the sensor 52. The transmitting and receiving fibers 47, 48 are guided to a scanning head 55 inside a flexible cable 54 as is a liquid supply line 53.

The scanning head consists of an elongated housing 56 which is preferably cylindrical and has a core 58 therein. The core 58 has a cavity 59, e.g., a bore, into which the liquid supply line 53 opens. An optical system 57 is located at the upper end of the cavity 59 and the end faces of the transmitting and receiving light conductors 47, 48 are adjacent to the optical system 57; the ends of the light conductors 47, 48 are suitably held in the core 58 for this purpose. The lower end of the cavity 59 is closed by a nozzle 60. Upon introduction of the scanning liquid into the cavity 59 under pressure, a fine scanning stream 61 is formed from the scanning liquid by the nozzle 60 and impinges on an object 62 at the scanning point 63. If light from the diode laser 45 is simultaneously conducted through the transmitting fiber 47, then the optical system 57 incorporates the transmitted light in the scanning stream 61. Return conduction of the reflected light and evaluation of the same occurs as described for FIG. 1.

Figure 7:
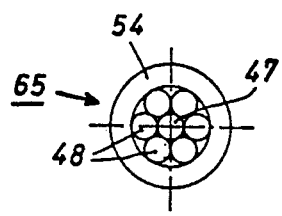

FIG. 7 is a plan view of the end face 65 of the fiber bundle which is formed from the transmitting and receiving fibers 47, 48 and is located above the optical system 57 of FIG. 6. The single light conductor 47 here serves as a transmitting fiber and is surrounded by a plurality of receiving fibers 48 arranged in a circle.

Figure 8:
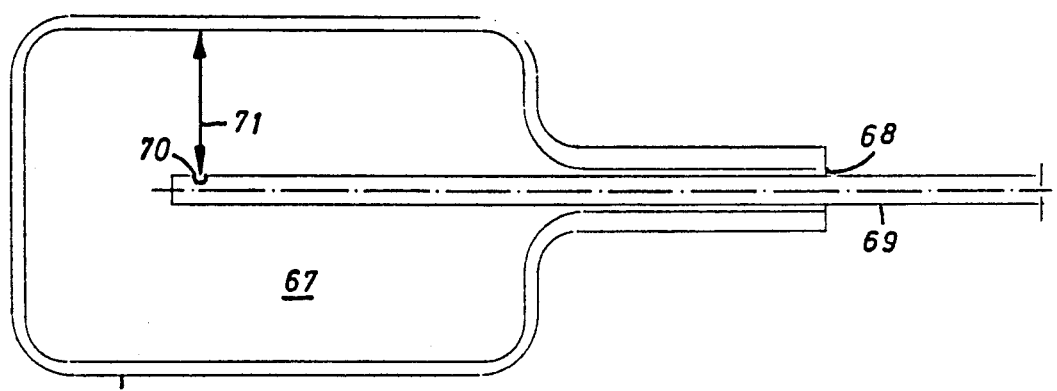
Figure 9:
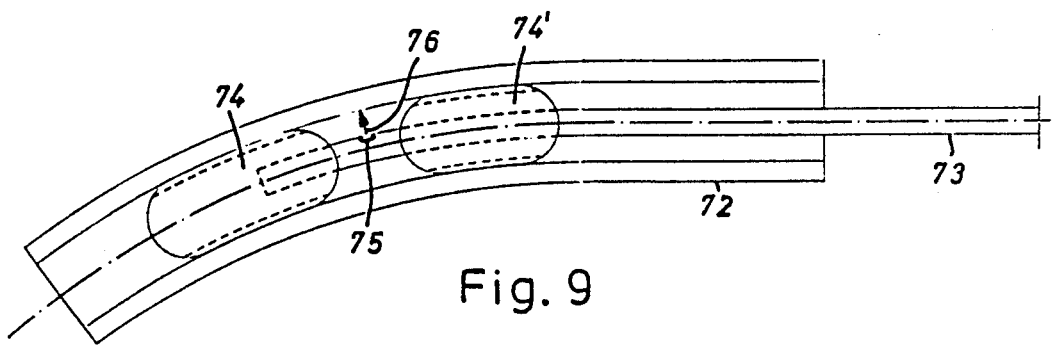
Figure 10:
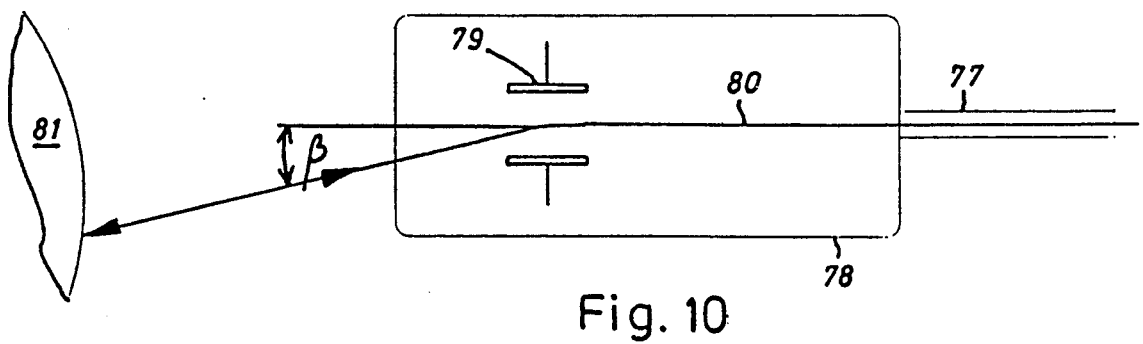

FIGS. 8 to 10 illustrate examples of the device which are adjusted to various products. In FIG. 8, the scanning head consists of a scanning tube 69 which is closed at its lower end. A peripheral nozzle 70 for discharge of a scanning stream 71 is arranged at the circumference of the scanning tube. The scanning tube 69 extends into a body 66 having a cavity 67 with an inner wall to be scanned. If the scanning tube 69 is turned during the scanning procedure while being slowly pushed into the cavity 67, the entire inner wall can be imaged, e.g., spirally.

FIG. 9 shows the design of the scanning head as a flexible scanning hose 73 provided, at its front end, with two spaced guide members 74, 74' serving to guide the scanning hose 73 in an elongated hollow body 72 which can be a curved tube. The lower end of the scanning hose 73 is closed and its circumferential wall has a peripheral nozzle 75 for the production of a scanning stream 76 between the two guide members 74, 74'. Upon insertion of the scanning hose 73 in the hollow body 72, the inner wall of the latter can be scanned along the line traveled by the scanning stream 76.

FIG. 10 illustrates a scanning head 77 the lower end of which extends into a chamber 78 containing a deflecting instrument 79. This deflecting instrument 79 serves to deflect the scanning stream 80 which is accordingly directed onto an object 81 at an angle of deflection beta as referred to the direction of discharge of the scanning stream 80 from the scanning head 77. The scanning stream 80 passes through the deflecting instrument 79 which can operate electrically or mechanically. If the deflecting instrument 79 operates electrically, then the scanning liquid employed must not only be light-conducting but also capable of being electrically deflected. In this manner, the scanning stream 80 can be guided over the object 81 in a predetermined fashion by control of the deflecting instrument 79 so that no relative movement between the object itself and the scanning head is required here to collect information.

Industrial Utility

The invention is intended for the optical scanning of objects having interfering surface coatings which can be removed for a period of time or continuously by a liquid stream. Similarly, the scanning of objects having a critical consistency or geometry is possible using the invention, e.g., the scanning of powdered or particulate material, bulk materials, objects having a fibrous surface structure, secreting organic substances or liquids with suspended substances.

The invention is likewise suited for the local inspection of radioactive components which are located in a wet environment within a protected radiation area. This allows the local surface condition and the temperature to be determined. The invention can also be used in the wet treatment of reprographic materials which are located in an environment such as wetness, brine or foam, or in an enclosed processing line. Here, densitometric values are obtained as identification criteria.

Moreover, the invention can be used during the chemical treatment of textile materials in a processing line where the environment can consist of wetness, vapor, brine or foam bubbles. The identification criteria detected are stretching of the material over the width of the path of travel at different locations of the treatment zone, color, other defects, color defects or weaving defects.

In particular, the invention can be used with advantage wherever a cooling emulsion which has been enriched with finely divided material residues such as metal residues covers the immediate processing location of the object as is the case in many areas of technology where objects undergo material-removing operations. Cracks, chipped areas or other defects due to material processing can here be observed and detected directly at the location of engagement of the material-removing tool since the cooling emulsion is pushed away by the liquid stream and the processing point is thereby exposed.

Furthermore, the invention can advantageously be used during dressing of the warp threads in a processing line when the layer of threads is pressed by a calender. The environment can here be vapor, wetness or dissolved substances and the identification criterion a torn individual thread which is coiled around the calender.

LIST OF REFERENCE NUMERALS

1 Light Source
2 Optical System
3 Light Conductor (Transmitting Fiber)
4 Flexible Cable
5 Scanning Head
6 Housing
7 Cavity
8 Nozzle
9 Optical System
10 Light Conductor (Receiving Fiber)
11 Optical System
12 Sensor
13 Container
14 Conveying System (Pump)
15 Liquid Supply Line
16 Impingement Point
17 Liquid Stream (Scanning Stream)
18 Object
19,20 Directional Arrows
21 Surface of the Object
22 System Supply Unit
23 Signal Processing Instrument
24 Object
25,26 Scanning Heads
27 Light Source
28 Sensor
29 Scanning Liquid
30 Transmitted Light Conductor
31 Receiving Light Conductor
32 Liquid Supply Line
33 Scanning Stream
34 Common Light Conductor in both Directions
35 Deflecting instrument
36,36' Scanning Heads
37,38 Scanning Streams
39,39' Liquid Supply Lines
40 Scanning Head
41 Light Ray
42 Scanning Head
43 Sensor Panel
44 Detector Housing
45 Diode Laser
46 Plate
47 Transmitting Fibers
48 Receiving Fiber
49,49' Holder
50,50' End of the Fibers
51 Optical System
52 Sensor
53 Liquid Supply Line
54 Flexible Cable
55 Scanning Head
56 Housing
57 Optical System
58 Core
59 Bore
60 Nozzle
61 Liquid Stream
62 Object
63 Scanning Point
64 Tee
65 End Face of the Bundle of Transmitting and Receiving Fibers
66 Body
67 Cavity
68 Opening
69 Scanning Tube
70 Nozzle
71 Liquid Stream
72 Elongated Hollow Body
73 Flexible Scanning Hose
74,74' Guide Members
75 Nozzle
76 Liquid Stream
77 Scanning Hose
78 Chamber
79 Deflecting Instrument
80 Liquid Stream
81 Object

I claim:

1. Process for the optical scanning of an object using a fine light beam which is moved relative to the object and is conducted into a light-conducting liquid, and an opto-electrical sensing and analyzing instrument for analyzing the reflected light, characterized in that the liquid is subject to a hydrodynamic pressure or an acceleration and a liquid stream (17,33,37,38,61,71, 76,80), which is directed onto the object (18,24,62, 66,72,81) to be scanned and rinses the same at the scanning location (16,63), is generated, the light being incorporated in the liquid stream and being directed within the same onto the impingement point (16,63) of the liquid stream upon the object, and the reflected light thereafter being conducted back within the liquid stream, separated from the same and delivered to the sensing and analyzing instrument (12,22;28;43;52).

2. Device for carrying out the process according to claim 1 characterized by the combination of a solid light conductor, a liquid light conductor in the form of a liquid stream which is directed onto the object at the scanning point, and an instrument for incorporating the transmitted light in the liquid stream and for separating the reflected light from the liquid stream.

3. Device for the optical scanning of an object using a fine light beam which is movable relative to the object and can be conducted into a light-conducting liquid, and an opto-electrical sensing and analyzing instrument for analyzing the reflected light, characterized by (a) a scanning head (5,25,26,36,36',40,42,55, 69,73,77) which has a nozzle (8,60,70,75) and is near the object (18,24,62,66,72,81)

(b) a conveying system (14) which conveys the light-conducting liquid to the scanning head (5,25,26, 36,36',40,42,55,69,73,77) from a container (13)

(c) the liquid being subjected to a pressure or an acceleration, being formed into a liquid stream (17,33,37,38,61,71,76,80) by the nozzle (8,60,70,75) and directed onto the object (18,24,62,66,72,81)

(d) an instrument (9,57) within the scanning head for incorporating the transmitted light in the liquid stream and/or separating the reflected light from the liquid stream in order to deliver the reflected light to the sensing and analyzing instrument (12,33;28,43,52).

4. Device according to claim 3, characterized in that the scanning head (5,55) has a cavity (7,59) into which a supply line (15,53) from the conveying system (14) opens, the instrument (9,57) for incorporating and/or separating the light being disposed above the nozzle (8,60,70.75) and being an optical system.

5. Device according to claim 4, characterized in that the light source (27) for generating the transmitted light and/or the sensing instrument (28) for receiving the reflected light is located within the scanning head (26).

6. Device according to claim 4, characterized in that the optical system (9,57) for incorporating and/or separating is located directly above the nozzle (8,60) of the scanning head (5,55) in the direction of the liquid stream (17,61) and in the upper portion of the cavity (7,59).

7. Device according to claim 3, characterized in that the scanning head (36,36';42) is provided with a plurality of nozzles for generating a plurality of liquid streams (33,37,38) and each has a light source (27), an instrument for incorporating or separating the light and a sensing and analyzing instrument (28,43) associated therewith.

8. Device according to claim 3, characterized by at least one transmitting and/or receiving optical fiber (3,30,34,47;10,31,34,48) which is arranged between the light source (1,27,45) and the scanning head (5,26,36,36',40,42,55,69,73,77) or between the sensing and analyzing instrument (11,23;28;43;52) and the scanning head (5,26,36,36',40,42,55,69,73,77), extends into the latter and terminates above the instrument (9,57) for incorporating and/or separating.

9. Device according to claim 3, characterized in that the scanning head consists of a tube (69,73) into which the liquid is conducted and which is closed at its lower end, the nozzle (70,75) being peripherally disposed at the circumference of the tube.

10. Device according to claim 3, characterized by an electrically or mechanically operating deflecting instrument (79) for the liquid stream (80) which is arranged behind the scanning head (77) and through which the liquid stream (80) passes for controlled deflection thereof.

11. Process for the optical scanning of an object using a fine light beam which is moved relative to the object and is conducted from the object in a light-conducting liquid, and an opto-electrical sensing and analyzing instrument for analyzing the reflected light, characterized in that the liquid is subject to a hydrodynamic pressure or an acceleration and a liquid stream, which is directed onto the object to be scanned and rinses the same at the scanning location, is generated, the light being directed toward the impingement point of the liquid stream upon the object from outside the liquid stream at an angle greater than zero, and the reflected light thereafter being incorporated into the liquid stream at the impingement point and being conducted within the liquid stream, separated from the same and delivered to the sensing and analyzing instrument.

12. Device for the optical scanning of an object using a fine light beam which is movable relative to the object and can be conducted into a light-conducting liquid, and an opto-electrical sensing and analyzing instrument for analyzing the reflected light, characterized by two scanning heads which have nozzles and are near the object, a conveying system which conveys the light-conducting liquid to the scanning heads from a container, the liquid being subjected to a pressure or an acceleration, being formed into two liquid streams by the nozzles and the two streams being directed onto the same point of the object, a first instrument within one scanning head for incorporating the transmitted light in the respective liquid stream for impingement upon and reflection at said point of the object, and a second instrument within the other scanning head for separating the reflected light from the respective liquid stream in order to deliver the reflected light to the sensing and analyzing instrument.

* * * * *